United States Patent
Endo et al.

(10) Patent No.: US 10,074,156 B2
(45) Date of Patent: Sep. 11, 2018

(54) IMAGE PROCESSING APPARATUS WITH DEFORMATION IMAGE GENERATING UNIT

(71) Applicant: CANON KABUSHIKI KAISHA, Tokyo (JP)

(72) Inventors: Takaaki Endo, Urayasu (JP); Kiyohide Satoh, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/103,464

(22) PCT Filed: Dec. 26, 2014

(86) PCT No.: PCT/JP2014/084758
§ 371 (c)(1),
(2) Date: Jun. 10, 2016

(87) PCT Pub. No.: WO2015/107866
PCT Pub. Date: Jul. 23, 2015

(65) Prior Publication Data
US 2016/0307292 A1   Oct. 20, 2016

(30) Foreign Application Priority Data

Jan. 16, 2014 (JP) ................. 2014-006214
Nov. 12, 2014 (JP) ................. 2014-230104

(51) Int. Cl.
G06K 9/00 (2006.01)
G06T 3/00 (2006.01)
(Continued)

(52) U.S. Cl.
CPC .......... G06T 3/0093 (2013.01); A61B 5/0035 (2013.01); A61B 5/0053 (2013.01);
(Continued)

(58) Field of Classification Search
CPC ......... G06T 7/0014; G06T 2207/10088; G06T 7/0012; G06T 2207/30068; G06T 2210/41;
(Continued)

(56) References Cited

U.S. PATENT DOCUMENTS 9,123,096 B2     9/2015  Miyasa et al. ......... G06T 7/0012
2008/0292164 A1* 11/2008  Azar ..................... A61B 5/0091
                                                         382/131
(Continued)

FOREIGN PATENT DOCUMENTS

CN   101511273 A    8/2009
CN   102727258 A   10/2012
(Continued)

OTHER PUBLICATIONS

Y. Hu et al., "A Statistical Motion Model Based on Biomechanical Simulations", Proc. MICCAI 2008, Part I, LNCS 5241, pp. 737-744 (2008).
(Continued)

Primary Examiner — Vu Le
Assistant Examiner — Guillermo Rivera-Martinez
(74) Attorney, Agent, or Firm — Fitzpatrick Cella Harper and Scinto

(57) ABSTRACT

An image processing apparatus comprising: medical image obtaining means for obtaining a medical image of an object in a first shape state; deformation information obtaining means for obtaining deformation information indicating deformation of the object from the first shape state to a second shape state; imaging region setting means for setting an imaging region of the object in the second shape state; deformation image generating means for generating a conversion image by converting the medical image deformed based on the deformation information in accordance with the (Continued)

imaging region; and display image generating means for generating a display image by overlapping the conversion image and the imaging region.

19 Claims, 14 Drawing Sheets

(51) Int. Cl.
| | |
|---|---|
| G16H 50/50 | (2018.01) |
| A61B 5/055 | (2006.01) |
| A61B 6/00 | (2006.01) |
| A61B 8/08 | (2006.01) |
| A61B 8/00 | (2006.01) |
| A61B 5/00 | (2006.01) |
| G06T 19/20 | (2011.01) |
| A61B 6/03 | (2006.01) |
| G06T 7/00 | (2017.01) |
| G06F 19/00 | (2018.01) |

(52) U.S. Cl.
CPC .......... *A61B 5/0095* (2013.01); *A61B 5/055* (2013.01); *A61B 5/4312* (2013.01); *A61B 5/708* (2013.01); *A61B 6/032* (2013.01); *A61B 6/037* (2013.01); *A61B 6/4417* (2013.01); *A61B 6/502* (2013.01); *A61B 6/5247* (2013.01); *A61B 8/0825* (2013.01); *A61B 8/4416* (2013.01); *A61B 8/483* (2013.01); *A61B 8/5261* (2013.01); *G06F 19/3437* (2013.01); *G06T 7/0012* (2013.01); *G06T 19/20* (2013.01); *G16H 50/50* (2018.01); *G06T 2207/10088* (2013.01); *G06T 2207/30068* (2013.01); *G06T 2210/41* (2013.01); *G06T 2219/2021* (2013.01)

(58) Field of Classification Search
CPC .......... G06T 3/0093; G06T 2219/2021; G06T 19/00; A61B 5/0091
See application file for complete search history.

(56) References Cited

U.S. PATENT DOCUMENTS

| | | | |
|---|---|---|---|
| 2009/0264758 A1 | 10/2009 | Fujita et al. | |
| 2010/0087733 A1 | 4/2010 | Nakajima et al. | 600/437 |
| 2010/0284591 A1* | 11/2010 | Arnon | A61B 5/015 |
| | | | 382/128 |
| 2011/0199390 A1 | 8/2011 | Iizuka et al. | 345/629 |
| 2011/0210261 A1* | 9/2011 | Maurer, Jr. | A61N 5/10 |
| | | | 250/393 |
| 2011/0216958 A1 | 9/2011 | Satoh et al. | 382/131 |
| 2011/0262015 A1* | 10/2011 | Ishikawa | G06K 9/6206 |
| | | | 382/128 |
| 2012/0114213 A1* | 5/2012 | Buelow | G06T 7/0032 |
| | | | 382/131 |
| 2012/0253173 A1 | 10/2012 | Endo et al. | |
| 2012/0262460 A1 | 10/2012 | Endo et al. | 345/441 |
| 2012/0321161 A1 | 12/2012 | Ishikawa et al. | 382/131 |
| 2013/0051646 A1 | 2/2013 | Nakano et al. | 382/131 |
| 2013/0165765 A1 | 6/2013 | Nishihara | 600/407 |
| 2013/0182901 A1 | 7/2013 | Ishida et al. | 382/103 |
| 2013/0188851 A1 | 7/2013 | Miyasa et al. | 382/131 |
| 2013/0267856 A1 | 10/2013 | Watanabe et al. | 600/476 |
| 2014/0037168 A1 | 2/2014 | Ishikawa et al. | 382/130 |
| 2016/0228075 A1* | 8/2016 | Kitamura | A61B 6/12 |

FOREIGN PATENT DOCUMENTS

| | | |
|---|---|---|
| EP | 2064996 | 6/2009 |
| JP | 2007-029353 | 2/2007 |
| JP | 2010-088627 | 4/2010 |
| JP | 2012-217769 | 11/2012 |
| JP | 2013-059658 | 4/2013 |
| WO | 2013/076616 A1 | 5/2013 |

OTHER PUBLICATIONS

C. Tanner et al., "Breast Shapes on Real and Simulated Mammograms", *Proc. Int. Workshop on Digital Mammography 2010* (IWDM 2010), LNCS 6136, pp. 540-547 (2010).

A.W.C. Lee et al., "Breast X-Ray and MR Image Fusion Using Finite Element Modeling", *Proc. Workshop on Breast Image Analysis in conjunction with MICCAI 2011*, pp. 129-136 (2011).

ESR dated Jul. 24, 2017 in counterpart Eur. Pat. Application 14878958.9 (in English).

* cited by examiner

IMAGE PROCESSING APPARATUS WITH DEFORMATION IMAGE GENERATING UNIT

TECHNICAL FIELD

The present invention relates to an image processing apparatus, an image diagnostic system, an image processing method, and a storage medium, and in particular to a technique to process medical images captured by various types of medical image acquisition apparatuses (modalities).

BACKGROUND ART

In recent years, photoacoustic tomography (PAT) imaging apparatuses (PAT apparatuses) have been developed in the medical field. PAT apparatuses excite absorbing materials inside an object by irradiating the object with optical pulses, and detect photoacoustic signals generated by thermoelastic expansion of the absorbing materials, so as to form images of properties of the object related to optical absorption. That is to say, images of an optical energy deposition amount distribution (optical energy absorption density distribution) inside the object with respect to irradiation light are formed. Also, based on this, images of an optical absorption coefficient distribution in the object related to an irradiation wavelength are formed. Furthermore, based on optical absorption coefficient distributions related to a plurality of wavelengths, images of the states of materials constructing the object (e.g., oxygen saturation of hemoglobin) can also be formed. These images are expected to make visible information related to new blood vessels generated inside and outside a tumor, such as cancer. Hereinafter, these images are collectively referred to as photoacoustic tomography images (PAT images).

With PAT apparatuses, irradiation is performed with near infrared ray pulses with a small energy, and therefore it is difficult to form images of deep parts of an object compared to the case of X-rays and like. In view of this, in Japanese Patent Laid-Open No. 2010-88627, imaging is performed in a state where a breast is held by two flat plates (hereinafter referred to as holding plates) and reduced in thickness in one form of a PAT apparatus using the breast as an object.

Japanese Patent Laid-Open No. 2007-29353 discloses a technique to display an X-ray irradiation field and an X-ray detection field as visually distinguishable pictures in such a manner that they are overlapped over an appearance image obtained by imaging a body surface of an object with a camera.

However, the technique of Japanese Patent Laid-Open No. 2010-88627 or Japanese Patent Laid-Open No. 2007-29353 is problematic in that, in a case where a region of attention in the object is not on the body surface but is inside the body of the object, an accurate range of the region of attention is unknown even with the use of marks on the body surface as reference information, and therefore it is difficult to appropriately set an imaging region.

In view of the above problem, the present invention provides a technique to set an imaging region such that a region of attention inside an object is imaged appropriately.

SUMMARY OF INVENTION

According to one aspect of the present invention, there is provided an image processing apparatus comprising: medical image obtaining means for obtaining a medical image of an object in a first shape state; deformation information obtaining means for obtaining deformation information indicating deformation of the object from the first shape state to a second shape state; imaging region setting means for setting an imaging region of the object in the second shape state; deformation image generating means for generating a conversion image by converting the medical image deformed based on the deformation information in accordance with the imaging region; and display image generating means for generating a display image by overlapping the conversion image and the imaging region.

Further features of the present invention will become apparent from the following description of exemplary embodiments (with reference to the attached drawings).

DESCRIPTION OF EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment: No Camera Image

An image processing apparatus according to the present embodiment assists in setting an imaging region of a PAT apparatus in which a breast is regarded as an object. A deformation MRI image (deformation image) is generated by deforming and positioning an MRI image with respect to a breast in an imaging state in which the breast is held by two flat plates (holding plates), and an imaging region is set on an imaging region setting screen displaying the deformation MRI image. The image processing apparatus according to the present embodiment will now be described.

<Configuration of Image Diagnostic System 1>

Figure 1:
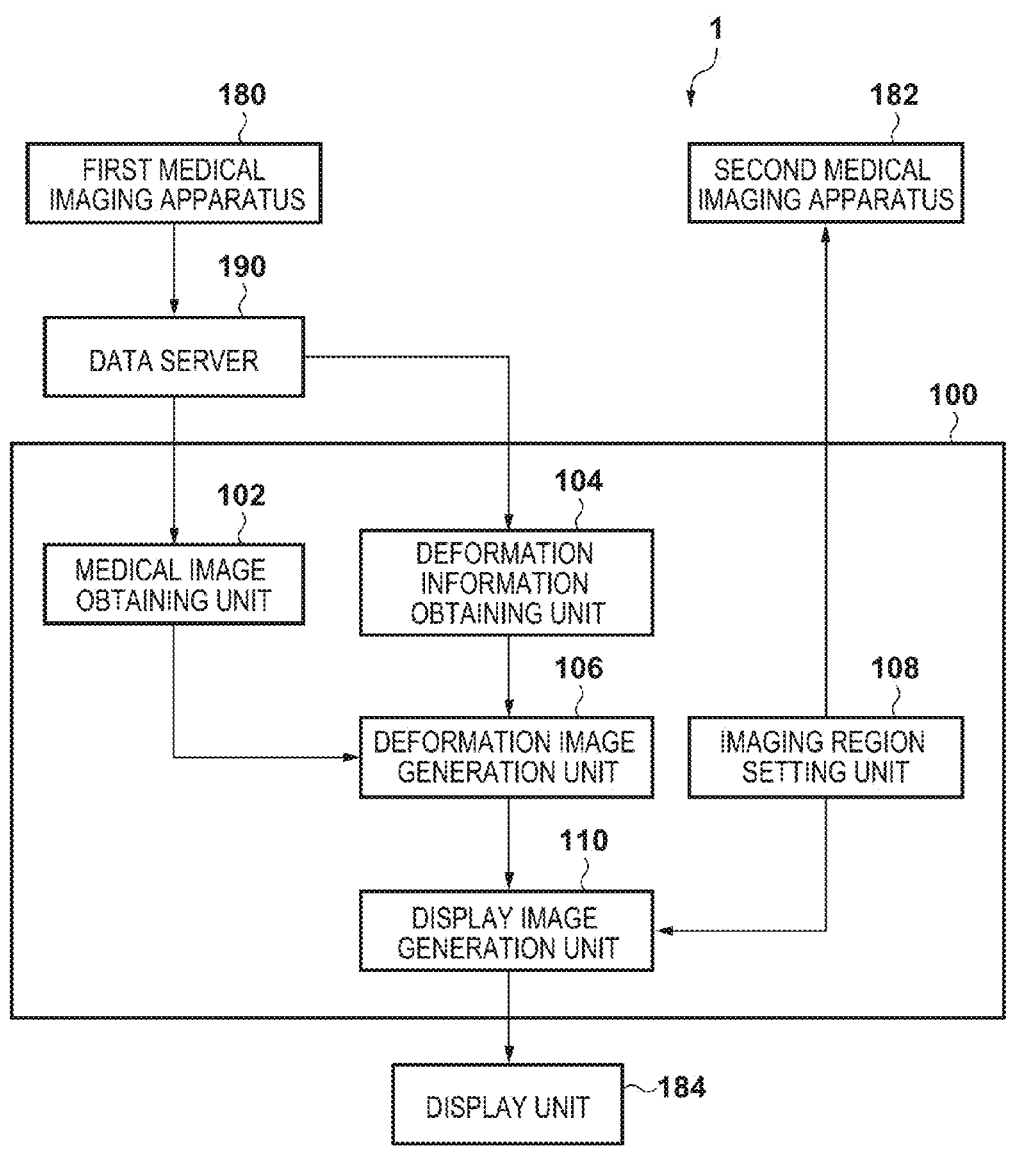
FIG. 1 shows functional configurations of an image diagnostic system and an image processing apparatus according to a first embodiment.

FIG. 1 shows a configuration of an image diagnostic system 1 according to the present embodiment. The image diagnostic system 1 includes an image processing apparatus 100, a first medical imaging apparatus 180, a second medical imaging apparatus 182, a display unit 184, and a data server 190. The image diagnostic system 1 is not limited to including these apparatuses and the like as constituent elements, and may additionally include other constituent elements or may not include a part of them.

Figure 2:
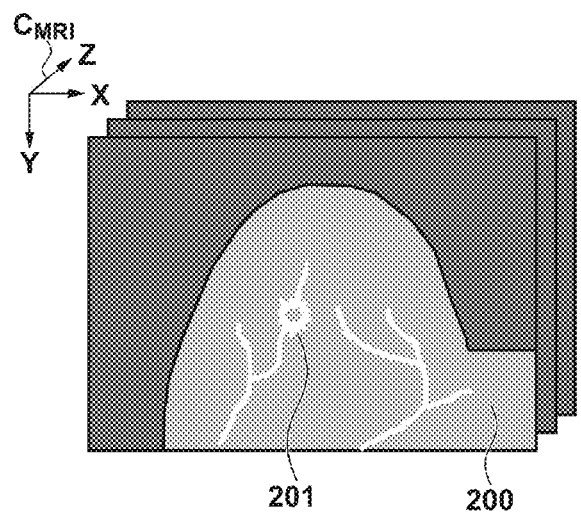
FIG. 2 is a schematic diagram showing an MRI image of an object.

The first medical imaging apparatus 180 is an MRI apparatus, and images a breast of an examinee in a prone position. FIG. 2 is a schematic diagram showing a two-dimensional image obtained by slicing a three-dimensional MRI image of the breast captured by the first medical imaging apparatus 180 along a cross-section perpendicular to a craniocaudal direction of the examinee (axial cross-section). It is assumed that, in the present embodiment, an MRI image coordinate system C_MRI is defined as follows: one point in an MRI image 200 is the origin, an axis representing a direction from the right hand to the left hand of the examinee is an X-axis, an axis representing a direction from the anterior side to the posterior side of the examinee is a Y-axis, and an axis representing a direction from the feet to the head of the examinee is a Z-axis.

Figure 3:
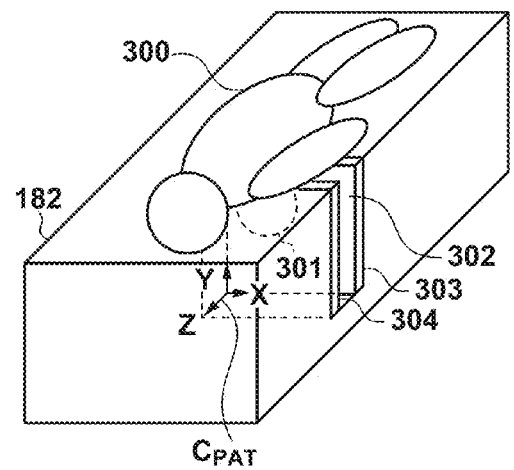
FIG. 3 is a schematic diagram showing a situation in which imaging is performed by a PAT apparatus according to the first embodiment.

The second medical imaging apparatus 182 is a photoacoustic tomography imaging apparatus (PAT apparatus), and images the breast of the examinee by performing irradiation with near infrared ray pulses within a range of an imaging region set by a later-described imaging region setting unit 108 of the image processing apparatus 100. FIG. 3 is a schematic diagram showing a situation in which imaging is performed by the second medical imaging apparatus 182. As shown in FIG. 3, an examinee 300 takes a prone position on a bed on an upper surface of the second medical imaging apparatus 182. An object, that is to say, a breast 301 on one side is inserted into an opening 302 of the upper surface of the second medical imaging apparatus 182. At this time, in order for irradiation light to reach the internal parts of the breast, the breast is held in a state where it is pressurized by two transparent holding plates (a holding plate 303 on the feet side and a holding plate 304 on the head side), and imaged in a state where the thickness thereof is reduced. It is assumed that, in the present embodiment, the holding plate 303 and the holding plate 304 are both flat plates, and surfaces thereof that come into contact with the breast (hereinafter referred to as holding surfaces) are planar surfaces.

Figure 4:
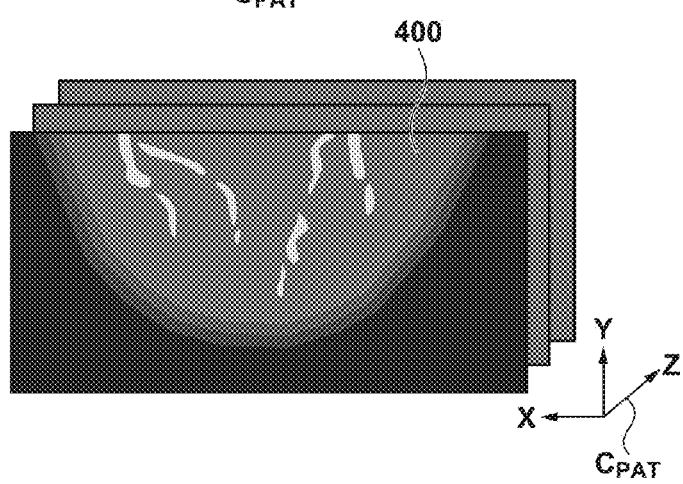
FIG. 4 is a schematic diagram showing a PAT image of the object.

The near infrared ray pulses, which represent irradiation light, are emitted by a non-illustrated light source in a direction orthogonal to the planar surfaces of the holding plates 303, 304. Photoacoustic signals generated inside the body in response to irradiation with the near infrared ray pulses are received by a non-illustrated ultrasound probe that is arranged to be orthogonal to the planar surfaces of the holding plates 303, 304. In the present embodiment, a PAT apparatus coordinate system C_PAT is defined as follows. A plane parallel to the holding plates 303, 304 is an XY-plane, an axis representing a direction from the right hand to the left hand of the examinee is an X-axis, and an axis representing a direction from the anterior side to the posterior side of the examinee is a Y-axis. Also, a normal direction of the holding plates 303, 304 is a Z-axis, and a direction from the feet to the head of the examinee is a positive direction along the Z-axis. In addition, a lower end position on the right-hand side of the inner planar surface of the holding plate 303 is the origin. FIG. 4 is a schematic diagram showing a two-dimensional image 400 obtained by slicing a three-dimensional PAT image of the breast captured by the second medical imaging apparatus 182 along a cross-section perpendicular to a craniocaudal direction of a human body (axial cross-section).

The display unit 184 includes an imaging region setting screen for setting an imaging region, and displays a display image generated by the image processing apparatus 100 on this screen. The data server 190 holds three-dimensional MRI images 200 obtained by the first medical imaging apparatus 180 imaging the breast of the examinee in a prone position, and these MRI images 200 are input to the image processing apparatus 100 via a later-described medical image obtaining unit 102 of the image processing apparatus 100.

<Configurations of Functional Blocks of Image Processing Apparatus 100>

The image processing apparatus 100 is connected to the data server 190, the second medical imaging apparatus 182, and the display unit 184. The image processing apparatus 100 includes the medical image obtaining unit 102, a deformation information obtaining unit 104, a deformation image generation unit 106, the imaging region setting unit 108, and a display image generation unit 110, and the operations of the functional blocks are controlled by a non-illustrated CPU reading and executing a program.

The medical image obtaining unit 102 obtains an MRI image 200 input to the image processing apparatus 100, and outputs this MRI image 200 to the deformation image generation unit 106. The deformation information obtaining unit 104 calculates and obtains deformation information by deforming and positioning the MRI image 200 with respect to the breast in the imaging state, and outputs this deformation information to the deformation image generation unit 106.

The deformation image generation unit 106 generates a deformation MRI image by deforming the MRI image 200 into the shape of the breast in the imaging state based on the MRI image 200 and the deformation information, and outputs the deformation MRI image to the display image generation unit 110. The imaging region setting unit 108 sets an imaging region based on user input to the imaging region setting screen of the display unit 184, and outputs the set imaging region to the second medical imaging apparatus 182 and the display image generation unit 110.

The display image generation unit 110 generates an MIP (maximum intensity projection) image (hereinafter referred to as a deformation MRI_MIP image) from the deformation MRI image, generates a display image based on the generated image and the imaging region, and outputs the display image to the display unit 184. It should be noted that the MIP image is also referred to as a maximum value projection image.

It should also be noted that the configurations of the above-described functional blocks are merely illustrative; a plurality of functional blocks may compose one functional block, and any of the functional blocks may be further divided into a plurality of functional blocks.

<Processing Executed by Image Processing Apparatus 100>

Figure 5:
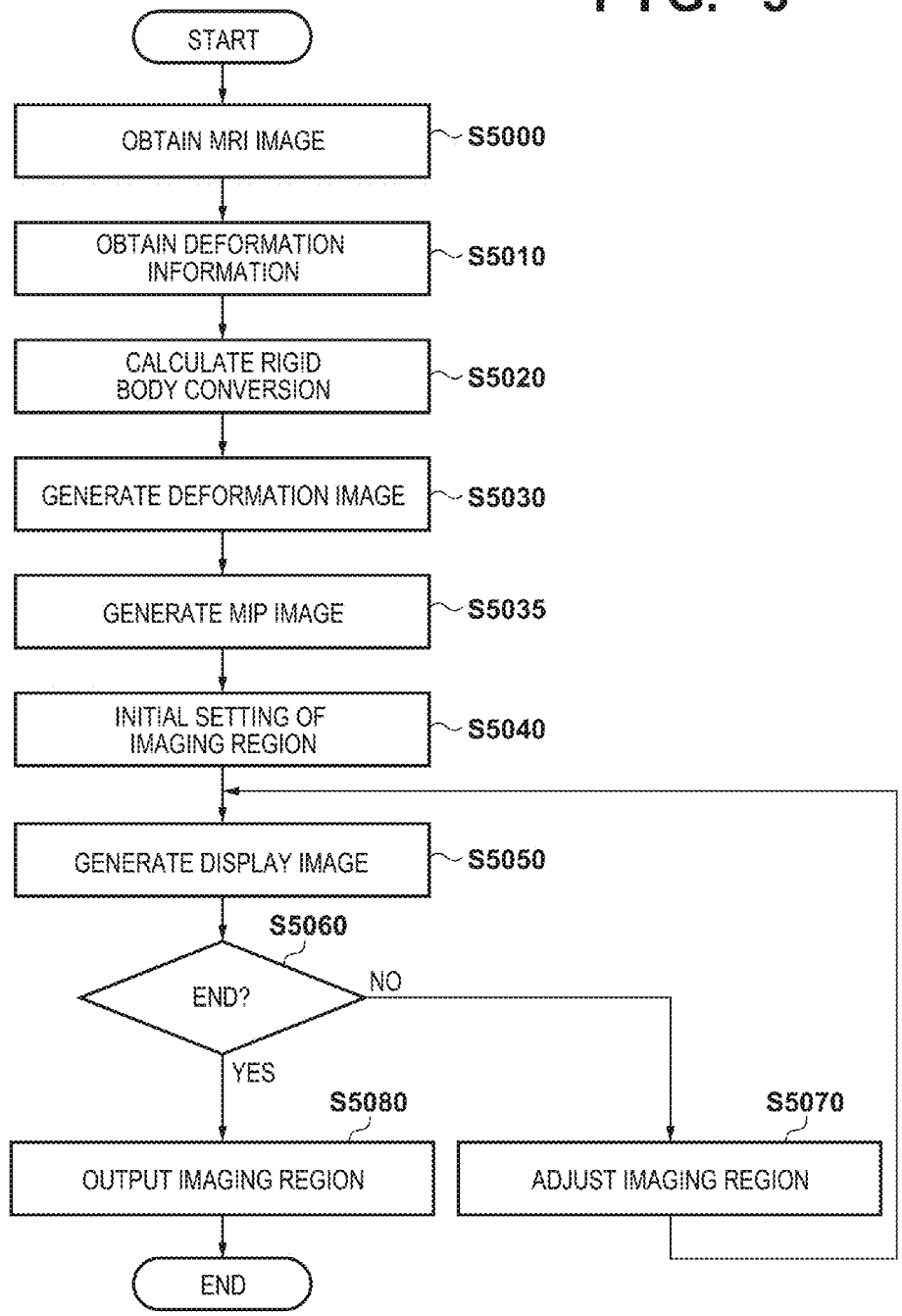
FIG. 5 is a flowchart showing a procedure of processing of the image processing apparatus according to the first embodiment.

Next, a description is given of a procedure of processing executed by the image processing apparatus 100 according to the present embodiment with reference to a flowchart of FIG. 5.

[Step S5000: Obtainment of MRI Image]

In step S5000, the medical image obtaining unit 102 obtains an MRI image 200 of a breast in a prone position input from the data server 190 to the image processing apparatus 100. It is assumed that, in the present embodiment, a nipple position in the MRI image 200 has been designated in advance.

[Step S5010: Obtainment of Deformation Information]

In step S5010, the deformation information obtaining unit 104 calculates deformation information for deforming the MRI image into the shape of the breast in the imaging state. It is assumed that, in the present embodiment, a deformation function F (x, y, z) representing deformation from a pre-hold state (a first shape state, an MRI state) to a post-hold state (a second shape state, the imaging state) is obtained by applying a physical deformation simulation to the MRI image, and this deformation function is used as the deformation information. The deformation function F (x, y, z) can be calculated using, for example, a physical deformation simulation technique disclosed in Angela Lee, et al., "Breast X-ray and MR image fusion using finite element modeling", Proc. Workshop on Breast Image Analysis in conjunction with MICCAI 2011, pp. 129-136, 2011. It should be noted that this document discloses a technique to position an X-ray mammography image obtained by imaging a breast pressurized by flat plates and an MRI image of the breast through a physical deformation simulation.

It should be noted that the present embodiment is based on the premise that the posture of the examinee in the PAT apparatus coordinate system C_PAT substantially matches the posture of the examinee in the MRI image coordinate system C_MRI. That is to say, it is assumed that the breast is compressed by the two holding plates 303, 304 along the Z-axis direction of the MRI image coordinate system C_MRI. It is also assumed that, at the time of the physical deformation simulation, a measured value of the distance between the two holding plates (the thickness of the post-hold breast), d, is input from the second medical imaging apparatus 182. It is further assumed that the deformation function F (x, y, z) is calculated such that the nipple position is the same in the pre-hold state and in the post-hold state.

[Step S5020: Calculation of Rigid Body Conversion]

In step S5020, the deformation image generation unit 106 obtains rigid body conversion between the MRI image coordinate system C_MRI and the PAT apparatus coordinate system C_PAT. That is to say, a coordinate conversion matrix T_MtoP from the MRI image coordinate system C_MRI to the PAT apparatus coordinate system C_PAT is derived. It is assumed that all of the coordinate conversion matrices described below, including T_MtoP, are 4×4 matrices representing translation and rotation of a coordinate system. The present embodiment is based on the premise that the posture of the examinee in the PAT apparatus coordinate system C_PAT substantially matches the posture of the examinee in the MRI image coordinate system C_MRI, and it is assumed that coordinate conversion from the MRI image coordinate system C_MRI to the PAT apparatus coordinate system C_PAT can be expressed only by way of translation. Under this premise, translational components of T_MtoP are calculated such that the nipple position in the MRI image obtained in step S5000 matches the nipple position of the examinee in the PAT apparatus coordinate system C_PAT.

Here, the nipple position in the PAT apparatus coordinate system C_PAT can be obtained using, for example, a non-illustrated ranging apparatus placed in a position in which the breast can be measured from a lower side of the opening 302 of the second medical imaging apparatus 182. That is to say, the nipple position in the PAT apparatus coordinate system C_PAT can be obtained by a user manually designating the nipple position in a range image of the breast captured by the ranging apparatus using a non-illustrated mouse, keyboard, and the like. It is assumed that, at this time, the ranging apparatus has already been calibrated in the PAT apparatus coordinate system C_PAT. It should be noted that the nipple position in the PAT apparatus coordinate system C_PAT is not limited to being obtained using the ranging apparatus, and may be obtained using apparatuses and means capable of measuring three-dimensional positions, such as a digitizer and a stereo camera.

[Step S5030: Generation of Deformation Image]

Figure 6:
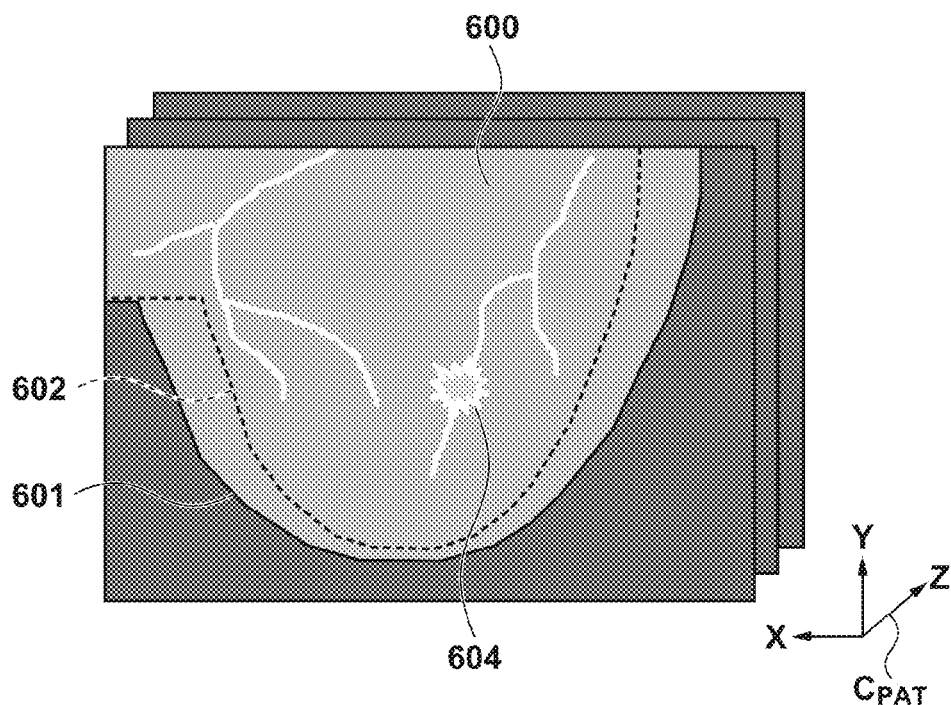
FIG. 6 is a schematic diagram showing a post-deformation MRI image.

In step S5030, based on the MRI image 200, the deformation image generation unit 106 generates a deformation MRI image that has been deformed into the shape of the breast in the imaging state. Specifically, deformation processing is applied to the MRI image 200 using the deformation function F (x, y, z) obtained in step S5010, and then conversion to the PAT apparatus coordinate system C_PAT is carried out using the rigid body conversion (coordinate conversion matrix T_MtoP) calculated in step S5030. As a result, a deformation MRI image in the PAT apparatus coordinate system C_PAT is generated. FIG. 6 is a schematic diagram showing a two-dimensional image obtained by slicing a deformation MRI image along an axial cross-section. As shown in FIG. 6, 600 denotes a deformation MRI image, 601 denotes a post-deformation breast region, and 602 denotes a pre-deformation breast shape. Also, 604 denotes a tumor in the deformation MRI image. Comparing the post-deformation breast region 601 with the pre-deformation breast shape 602, it is apparent that pressurization in the Z-axis direction of the PAT apparatus coordinate system C_PAT has caused the breast region to extend along the XY-plane and to compress in the Z-axis direction.

[Step S5035: Generation of MIP Image (Conversion Image)]

Figure 7:
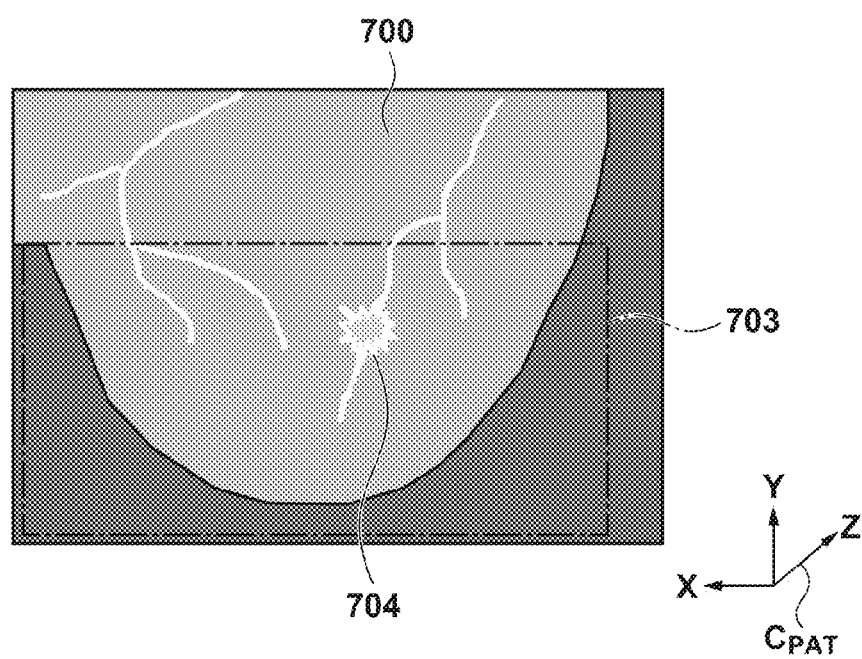
FIG. 7 is a schematic diagram showing an example of a display image according to the first embodiment.

In step S5035, the deformation image generation unit 106 generates a conversion image that has been converted in accordance with an imaging region. That is to say, the deformation image generation unit 106 generates a conversion image that has been converted in accordance with a space for setting the imaging region. Specifically, the deformation image generation unit 106 generates a conversion image by converting a deformation MRI_MIP image in accordance with the imaging region for the purpose of display on the imaging region setting screen of the display unit 184. For example, a deformation MRI_MIP image 700 shown in FIG. 7 is generated by projecting a maximum pixel value in the Z-axis direction of the PAT apparatus coordinate system C_PAT onto the XY-plane (Z=0) based on the deformation MRI image 600 generated in step S5030.

[Step S5040: Initial Setting of Imaging Region]

In step S5040, the imaging region setting unit 108 configures initial setting of an imaging region of the second medical imaging apparatus 182. For example, an oblong including the entirety of a range that can be imaged by the second medical imaging apparatus 182 is set as an initial value of the imaging region. It is assumed that, in the present embodiment, the imaging region is set in the PAT apparatus coordinate system C_PAT.

[Step S5050: Generation of Display Image]

In step S5050, the display image generation unit 110 generates a display image by overlapping an imaging region 703 shown in FIG. 7 over the deformation MRI_MIP image 700 generated in step S5035, and outputs the display image to the display unit 184.

Here, the imaging region 703 may be displayed in a frame line as shown in FIG. 7, and the inside of the region may be filled with a predetermined color and texture of predetermined transparency. Furthermore, the user may be enabled to adjust the type of the frame line, the filling color and texture, the transparency, and the like using the non-illustrated mouse, keyboard, and the like.

[Step S5060: End Determination]

In step S5060, the image processing apparatus 100 determines whether or not to end a process for setting the imaging region. For example, determination to end the process is input by an operator clicking an end button arranged on a non-illustrated monitor using the non-illustrated mouse. If the process is determined to be ended, processing proceeds to step S5080. On the other hand, if the process is not determined to be ended, processing proceeds to step S5070.

[Step S5070: Adjustment of Imaging Region]

In step S5070, based on a user operation, the imaging region setting unit 108 adjusts the imaging region of the second medical imaging apparatus 182 on the display image. Specifically, on an image displayed on the imaging region setting screen of the display unit 184, a range of the set imaging region 703 (two-dimensional rectangular region) is manually adjusted by the user using the non-illustrated mouse, keyboard, and the like. Based on information that the user has visually confirmed on the displayed image, the user adjusts the imaging region 703 such that it includes, for example, the entirety of a tumor 704. Thereafter, processing returns to step S5050.

[Step S5080: Output of Imaging Region]

In step S5080, the imaging region setting unit 108 outputs the imaging region to the second medical imaging apparatus 182. It should be noted that, in consideration of error in the deformation information calculated in step S5010, the imaging region output to the second medical imaging apparatus 182 may be adjusted to be larger than the imaging region 703 designated by the user. For example, a predetermined value may be added as a margin. Also, the deformation information calculated in step S5010 may include information related to error in calculation of the deformation information (e.g., a positioning residual), and the added margin may be decided on based on this information related to error. At this time, only the imaging region output to the second medical imaging apparatus 182 may be adjusted to be large, without adjusting the imaging region output to the display image generation unit 110 to be large. The processing sequence of the image processing apparatus 100 is executed in the above-described manner.

As described above, the image processing apparatus 100 according to the present embodiment includes the medical image obtaining unit 102 that obtains a medical image (the MRI image 200) of an object (e.g., a breast) in the first shape state (an unheld state), the deformation information obtaining unit 104 that obtains deformation information indicating deformation of the object from the first shape state (the unheld state) to the second shape state (a held state in which the object is held by the holding plates 303, 304), the imaging region setting unit 108 that sets an imaging region of the object in the second shape state (the imaging region 703), the deformation image generation unit 106 that generates a conversion image (the deformation MRI_MIP image 700) by converting a medical image deformed based on the deformation information (the deformation MRI image 600) in accordance with the imaging region (the imaging region 703), and the display image generation unit 110 that generates a display image by overlapping the conversion image (the deformation MRI_MIP image 700) and the imaging region (the imaging region 703).

In this way, when setting an imaging region of a PAT image, the image processing apparatus according to the present embodiment can refer to an MRI image in which a region of attention, such as a tumor, inside the object is rendered. This makes it possible to set the imaging region such that a region of attention, such as a tumor, inside the object can be imaged appropriately.

While the present embodiment has described an exemplary case in which a breast of a human body is regarded as an object, the present invention is not limited to being embodied in this way, and any object may be used.

First Modification Example of First Embodiment

While the present embodiment has described an exemplary case in which a deformation MRI_MIP image is generated as a conversion image, embodiments of the present invention are not limited in this way, and an axial cross-section (XY-plane) of a deformation MRI image and the like may be generated as a conversion image. At this time, an axial cross-section including the tumor 704 may be selected and displayed, or axial cross-sections between Z=0 and Z=d (the distance between the post-hold flat plates) may be displayed in sequence so as to enable confirmation of whether or not the entirety of the tumor 704 is included. Also, a conversion image is not limited to an axial cross-section of a deformation MRI image; a sagittal cross-section (YZ-plane) and a coronal cross-section (XZ-plane) of a deformation MRI image may be generated as a conversion image, and setting and confirmation of an imaging region may be enabled thereon. Furthermore, confirmation of an imaging region is not limited to being enabled on an axial cross-section, a sagittal cross-section, and a coronal cross-section of a deformation MRI image, and may be enabled on any cross-section including a curved cross-section. Also, a cross-sectional image according to the present modification example may be an MIP image (a slab MIP image) obtained by projecting a maximum pixel value within a predetermined range from a cross-section onto the cross-section.

Second Modification Example of First Embodiment

While the present embodiment has described an exemplary case in which a display image is generated based on a two-dimensional deformation MRI_MIP image and a two-dimensional imaging region, embodiments of the present invention are not limited in this way. For example, observation from any line-of-sight direction may be enabled by generating a volume rendering image of a three-dimensional deformation MRI image as a conversion image and generating a display image by overlapping a three-dimensional imaging region. That is to say, the deformation image generation unit 106 can generate a volume rendering image or a maximum value projection image (MIP image) of a medical image pertaining to a shape state of the object as a conversion image. It should be noted that a three-dimensional imaging region can be set as, for example, a cuboid region formed by pushing an imaging region (a rectangular region) on a two-dimensional plane at Z=0 in the PAT apparatus coordinate system C_PAT from Z=0 to Z=d.

Third Modification Example of First Embodiment

While the present embodiment has described an exemplary case in which an MRI apparatus is used as the first medical imaging apparatus 180, embodiments of the present invention are not limited in this way. For example, an X-ray CT apparatus, a PET/SPECT apparatus, a three-dimensional ultrasound apparatus, and the like can be used thereas. Also, any other modality may be used thereas. When these modalities are used, it is sufficient to obtain the deformation function F (x, y, z) by not only estimating deformation by pressurization with flat plates, but also estimating deformation caused by differences in a body position for imaging (e.g., gravitational deformation from a supine position to a prone position). It should be noted that gravitational deformation from a supine position to a prone position can be estimated using, for example, a method based on a gravitational deformation simulation disclosed in Y. Hu, et al., "A statistical motion model based on biomechanical simulations", Proc. MICCAI 2008, Part I, LNCS 5241, pp. 737-744, 2008. Also, the first medical imaging apparatus 180 and the second medical imaging apparatus 182 may be the same imaging apparatus. Furthermore, while the present embodiment has described an exemplary case in which a PAT apparatus is used as the second medical imaging apparatus 182, embodiments of the present invention are not limited in this way. For example, an X-ray mammography apparatus, an ultrasound diagnostic apparatus, and any other modality may be used thereas.

Fourth Modification Example of First Embodiment

While the present embodiment has described an exemplary case in which the deformation MRI image 600 is generated and a deformation MRI_MIP image is generated based thereon, embodiments of the present invention are not limited in this way. For example, a deformation MRI_MIP image may be generated based on the MRI image 200 and deformation information, without generating the deformation MRI image 600.

Second Embodiment: With Camera Image

An image processing apparatus according to the present embodiment assists in setting an imaging region on a PAT apparatus that is configured to image the appearance of a breast with a camera mounted on the PAT apparatus and to set an imaging region on that image (hereinafter referred to as an appearance image). That is to say, an MRI image is deformed in accordance with the breast in an imaging state so as to generate an image that shows the internal parts of the breast (including a region of attention, such as a tumor) in a see-through fashion over the appearance image of the breast in the imaging state, and the imaging region can be set on an imaging region setting screen displaying the generated image.

In the present embodiment, a deformation MRI image is generated by deforming and positioning an MRI image with respect to an appearance image, that is to say, by estimating deformation by pressurization with flat plates. Also, in the present embodiment, a region that is not appropriate for capturing of a PAT image (an inappropriate region) is set on an appearance image. The following describes the image processing apparatus according to the present embodiment, centering on differences from the first embodiment.

<Configuration of Image Diagnostic System 8>

Figure 8:
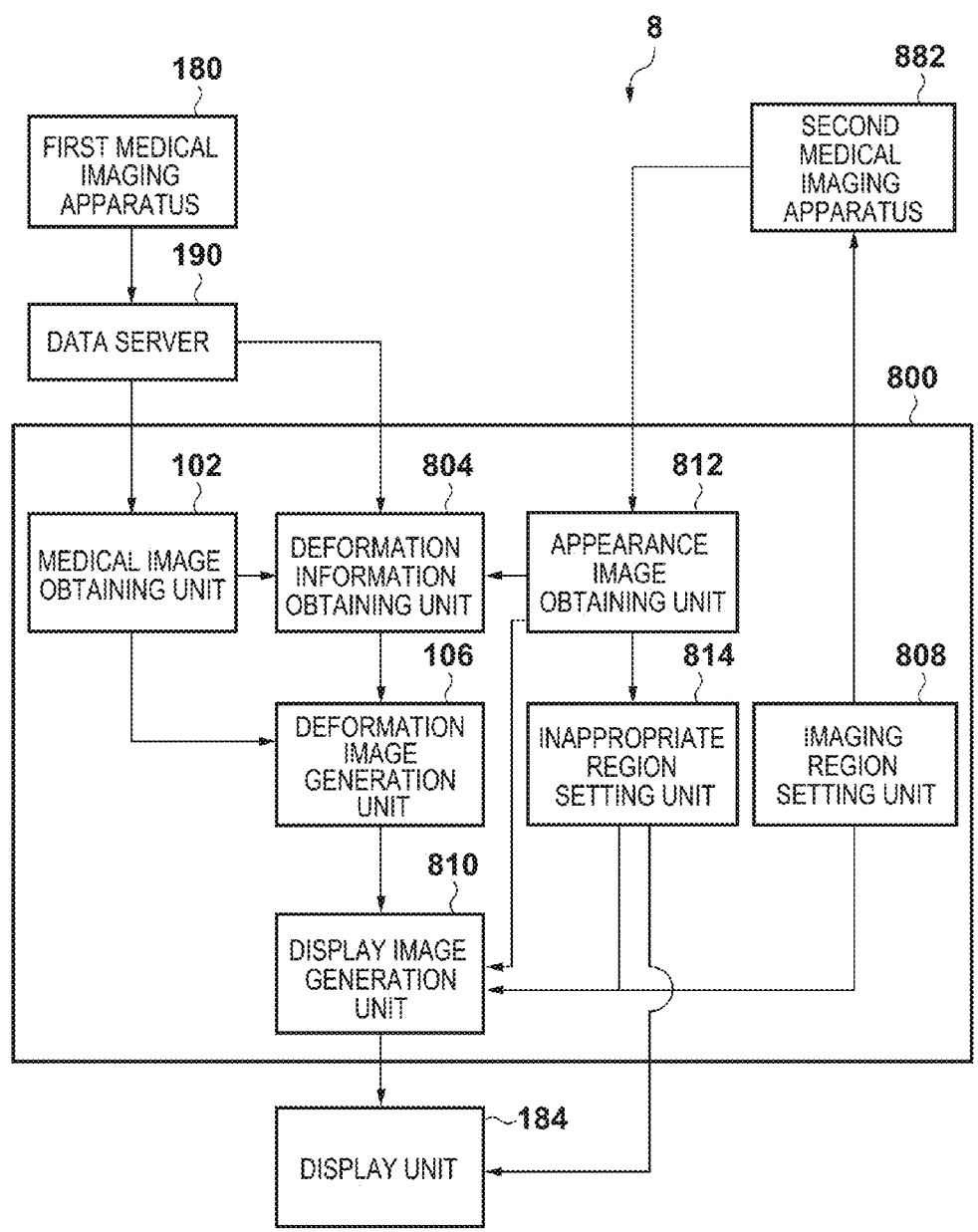
FIG. 8 shows functional configurations of an image diagnostic system and an image processing apparatus according to a second embodiment.

FIG. 8 shows a configuration of an image diagnostic system 8 according to the present embodiment. It should be noted that processing units that have the same functions as those in FIG. 1 are given the same numbers and signs thereas, and a description thereof is omitted.

The image diagnostic system 8 includes an image processing apparatus 800, a first medical imaging apparatus 180, a second medical imaging apparatus 882, a display unit 184, and a data server 190.

Figure 9:
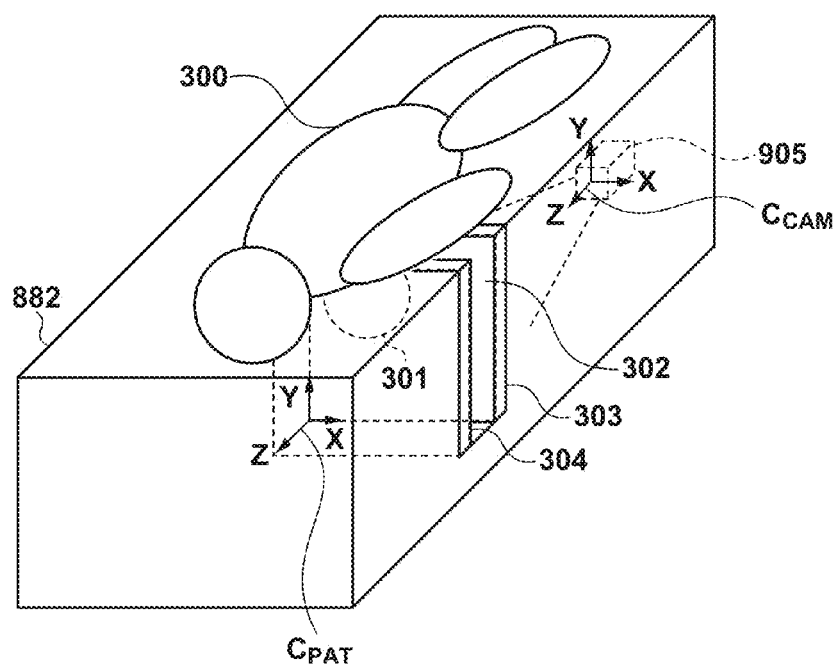
FIG. 9 is a schematic diagram showing a situation in which imaging is performed by a PAT apparatus according to the second embodiment.

The second medical imaging apparatus 882 is configured in the same manner as the second medical imaging apparatus 182, which has been described in the first embodiment with reference to FIG. 3, and additionally includes a camera for capturing an appearance image of a breast. FIG. 9 is a schematic diagram showing a situation in which imaging is performed by the second medical imaging apparatus 882. Referring to FIG. 9, 905 denotes a camera placed in a position in which the appearance of the breast can be imaged through a holding plate 303 from the feet side, and C_CAM denotes a camera coordinate system in which a position of a focal point of the camera 905 is the origin. It is assumed here that the camera 905 has already been calibrated in a PAT apparatus coordinate system C_PAT. It is also assumed that a coordinate conversion matrix T_CtoP from the camera coordinate system C_CAM to the PAT apparatus coordinate system C_PAT and internal parameters of the camera, which have been obtained through the camera calibration, are held by the image processing apparatus 800 as known information.

Figure 10:
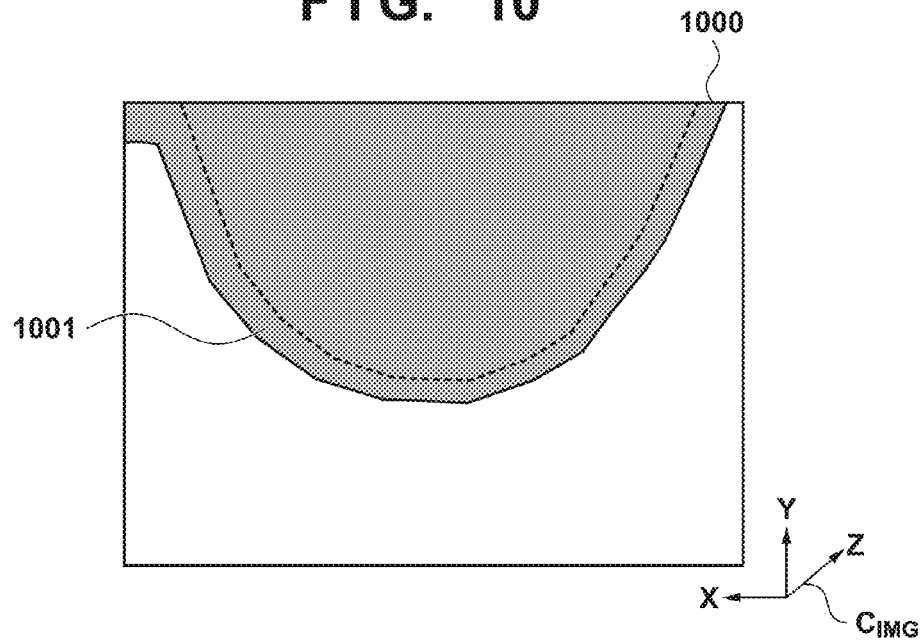
FIG. 10 is a schematic diagram showing an appearance image captured by a camera mounted on the PAT apparatus.

FIG. 10 is a schematic diagram showing an appearance image 1000 of the breast captured by the camera 905. It is assumed that, in the present embodiment, a lower right end of the appearance image 1000 is the origin of an appearance image coordinate system C_IMG, and the appearance image 1000 lies on a plane at Z=0. It should be noted that conversion from the camera coordinate system C_CAM to the appearance image coordinate system C_IMG can be carried out using general methods, and therefore a description thereof is omitted.

<Configurations of Functional Blocks of Image Processing Apparatus 800>

The image processing apparatus 800 is connected to the data server 190, the second medical imaging apparatus 882, and the display unit 184. The image processing apparatus 800 includes a medical image obtaining unit 102, a deformation information obtaining unit 804, a deformation image generation unit 106, an imaging region setting unit 808, a display image generation unit 810, an appearance image obtaining unit 812, and an inappropriate region setting unit 814.

The deformation information obtaining unit 804 obtains deformation information by deforming and positioning an MRI image 200 with respect to the appearance image 1000, and outputs the deformation information to the deformation image generation unit 106.

The imaging region setting unit 808 sets an imaging region on an imaging region setting screen of the display unit 184, and outputs the set imaging region to the second medical imaging apparatus 882 and the display image generation unit 810.

The display image generation unit 810 generates a deformation MRI_MIP image from a deformation MRI image 600, generates a display image based on the generated image, the appearance image 1000, an inappropriate region 1001 shown in FIG. 10 that is not appropriate for capturing of a PAT image, and the imaging region, and outputs the display image to the display unit 184.

The appearance image obtaining unit 812 obtains an appearance image input to the image processing apparatus 800, and outputs the appearance image to the inappropriate region setting unit 814, the deformation information obtaining unit 804, and the imaging region setting unit 808.

The inappropriate region setting unit 814 sets, on the appearance image displayed on the imaging region setting screen of the display unit 184, a region that is not appropriate for capturing of a PAT image (an inappropriate region), and outputs the inappropriate region to the imaging region setting unit 808.

It should be noted that the configurations of the above-described functional blocks are merely illustrative; a plurality of functional blocks may compose one functional block, and any of the functional blocks may be further divided into a plurality of functional blocks.

<Processing Executed by Image Processing Apparatus 800>

Figure 11:
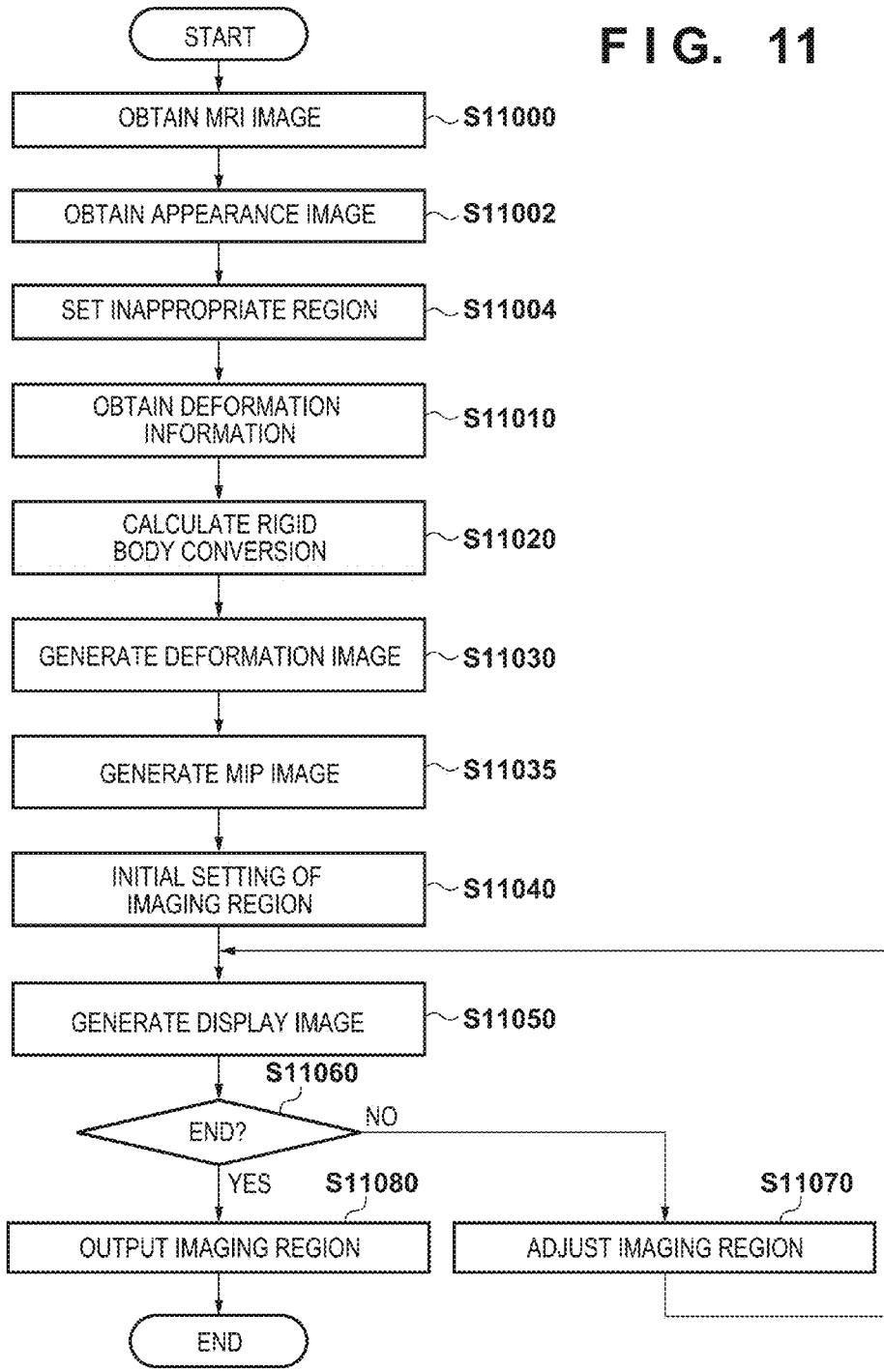
FIG. 11 is a flowchart showing a procedure of processing of the image processing apparatus according to the second embodiment.

Next, a description is given of a procedure of processing executed by the image processing apparatus 800 according to the present embodiment with reference to a flowchart of FIG. 11.

Compared to the processing executed by the image processing apparatus 100 according to the first embodiment, which has been described with reference to FIG. 5, the processing according to the present embodiment differs in that step S11002 and step S11004 intervene between a process of step S11000 and a process of step S11010. The processing according to the present embodiment also differs in that processes of step S11010, step S11035 to step S11050, and step S11070 are executed in place of the processes of step S5010, step S5035 to step S5050, and step S5070, respectively. The following description centers on the processes of these steps. It should be noted that processes of step S11000, step S11020, step S11030, step S11060, and step S11080 are similar to the processes of step S5000, step S5020, step S5030, step S5060, and step S5080, respectively, and therefore a description thereof is omitted.

[Step S11002: Obtainment of Appearance Image]

In step S11002, the appearance image obtaining unit 812 obtains an appearance image 1000 of a breast of an examinee input from the second medical imaging apparatus 882 to the image processing apparatus 100.

[Step S11004: Setting of Inappropriate Region]

In step S11004, the inappropriate region setting unit 814 displays the appearance image 1000 on the imaging region setting screen of the display unit 184, and sets an inappropriate region that is not appropriate for capturing of a PAT image on the displayed image. In the present embodiment, a region in which appropriate capturing of a PAT image is assumed to fail because, for example, the breast is not pressurized appropriately is set as an inappropriate region.

For example, 1001 in FIG. 10, which is a region between a dash line and a solid line, denotes an inappropriate region. A user can manually set such an inappropriate region using a non-illustrated mouse, keyboard, and the like. Alternatively, such an inappropriate region may be automatically set using image processing and the like.

[Step S11010: Obtainment of Deformation Information]

In step S11010, the deformation information obtaining unit 804 obtains deformation information for deforming the MRI image into the shape of the breast in the imaging state. It is assumed that, in the present embodiment, a deformation function F (x, y, z) is obtained by deforming and positioning the MRI image 200 with respect to the appearance image 1000, and this deformation function is used as the deformation information. This positioning can be performed using, for example, a technique disclosed in C. Tanner, et al., "Breast Shapes on Real and Simulated Mammograms", Proc. Int. Workshop on Digital Mammography 2010 (IWDM 2010), LNCS 6136, pp. 540-547, 2010 in which a post-deformation breast shape, which is obtained by applying to an MRI image a simulation of physical deformation caused by pressurization with flat plates, is evaluated based on a two-dimensional breast shape extracted from an X-ray mammography image.

[Step S11035: Generation of MIP Image]

Figure 12:
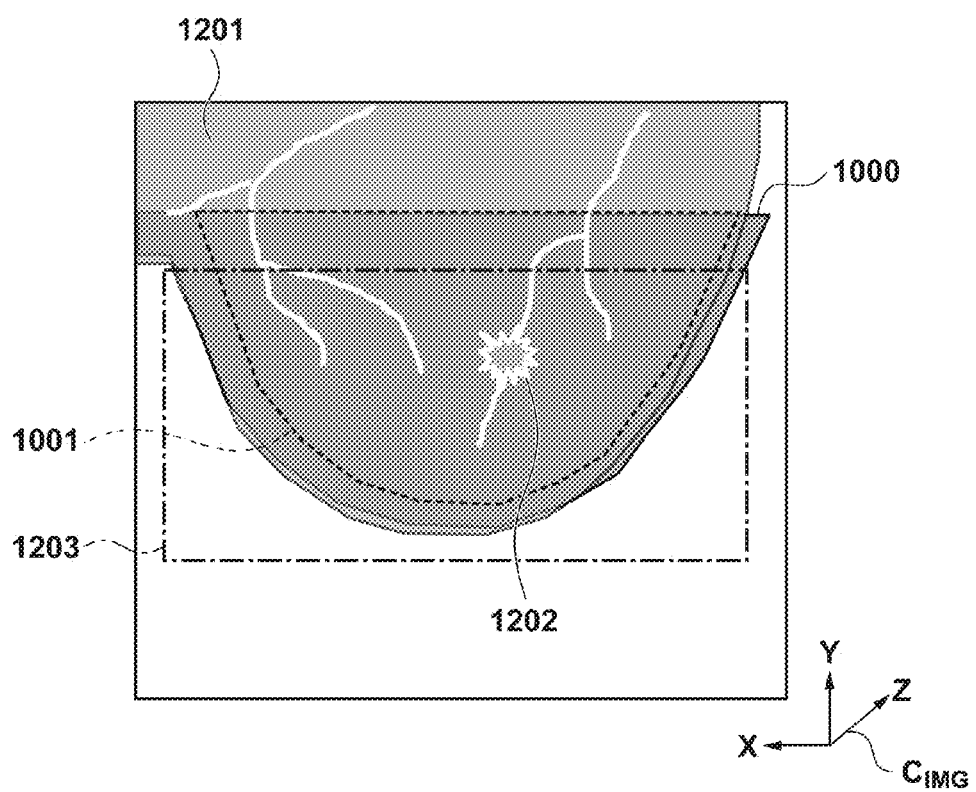
FIG. 12 is a schematic diagram showing an example of a display image according to the second embodiment.

In step S11035, the display image generation unit 810 generates a conversion image that has been converted in accordance with a space for setting the imaging region (a plane of the appearance image). First, the deformation MRI image 600 in the PAT apparatus coordinate system C_PAT, which was generated in step S11030, is converted for the camera coordinate system C_CAM, and then further converted for the appearance image coordinate system C_IMG. Next, a deformation MRI_MIP image 1201 in the appearance image coordinate system C_IMG is generated as a conversion image by projecting a maximum pixel value in a Z-axis direction of the appearance image coordinate system C_IMG onto an XY-plane (Z=0) (see FIG. 12).

[Step S11040: Initial Setting of Imaging Region]

In step S11040, the imaging region setting unit 808 configures initial setting of an imaging region of the second medical imaging apparatus 882. For example, an oblong including the entirety of a range that can be imaged by the second medical imaging apparatus 882 is set as an initial value of the imaging region. It is assumed that, in the present embodiment, the imaging region is set in the appearance image coordinate system C_IMG.

Next, based on the initial value of the imaging region in the appearance image coordinate system C_IMG, an imaging region in the PAT apparatus coordinate system C_PAT is obtained. For example, four vertices of the set imaging region are converted into four points in the camera coordinate system C_CAM, four intersections between the holding plate 303 and four straight lines connecting these four points and the origin of the camera coordinate system are obtained, and the four intersections are converted into four points in the PAT apparatus coordinate system C_PAT. Then, a rectangle circumscribing these four points is regarded as an imaging region 1203 in the PAT apparatus coordinate system C_PAT (see FIG. 12).

[Step S11050: Generation of Display Image]

In step S11050, the display image generation unit 810 generates a display image by overlapping the deformation MRI_MIP image 1201 generated in step S11035, the inappropriate region 1001, and the imaging region 1203 over the appearance image 1000, and outputs the display image to the display unit 184. In this case, a space for setting the imaging region is a plane of the appearance image 1000. It should be noted that the inappropriate region 1001 may not overlap. That is to say, the display image generation unit 810 may generate the display image by overlapping the appearance image 1000, the conversion image (deformation MRI_MIP image 1201), and the imaging region 1203.

It should be noted that the deformation MRI_MIP image 1201 may overlie the appearance image 1000 in a semi-transparent fashion or at a transparency of 0%. Alternatively, the user may be enabled to adjust the transparency using the non-illustrated mouse, keyboard, and the like.

[Step S11070: Adjustment of Imaging Region]

In step S11040, the imaging region setting unit 808 adjusts the imaging region of the second medical imaging apparatus 882. Specifically, first, on an image displayed on the imaging region setting screen of the display unit 184, the user manually adjusts a range of the set imaging region 1203 (two-dimensional rectangular region) using, for example, the non-illustrated mouse, keyboard, and the like. The user adjusts the imaging region 1203 such that it includes, for example, the entirety of a tumor 1202. Then, based on the imaging region 1203 in the appearance image coordinate system C_IMG, an imaging region in the PAT apparatus coordinate system C_PAT is obtained through a process similar to step S11040. Thereafter, processing returns to step S11050. The processing sequence of the image processing apparatus 800 is executed in the above-described manner.

As described above, when setting an imaging region of a PAT image, the image processing apparatus according to the present embodiment can refer to an MRI image and an appearance image of a breast together. This makes it possible to set an imaging region such that a region of attention, such as a tumor, in an object can be imaged more appropriately.

First Modification Example of Second Embodiment

While the present embodiment has described a case in which the camera 905 is placed in a position in which the appearance of a breast can be imaged through the holding plate 303 from the feet side, embodiments of the present invention are not limited in this way. For example, it may be arranged in a position in which the appearance of the breast can be imaged through a holding plate 304 from the head side, a position in which the appearance of the breast can be imaged laterally, and the like. Also, the number of placed cameras is not limited to one, and may be more than one; at this time, a display image may be generated for each of appearance images captured by the respective cameras.

Second Modification Example of Second Embodiment

While the present embodiment has described an exemplary case in which an inappropriate region and an imaging region are set on an image in the appearance image coordinate system C_IMG, embodiments of the present invention are not limited in this way, and an inappropriate region and an imaging region may be set on an image in the PAT apparatus coordinate system C_PAT. In this case, it is sufficient to convert the appearance image 1000 and the inappropriate region 1001 from the appearance image coordinate system C_IMG into the camera coordinate system C_CAM through, for example, planar projective conversion of four points at four corners of the holding plate 303, and then further convert them into the PAT image coordinate system C_PAT. It should be noted that modification examples similar to those of the first embodiment are applicable in the present embodiment.

Third Embodiment

While the first and second embodiments have described an exemplary case in which a PAT apparatus used as the second medical imaging apparatus 182 adopts a scheme whereby an object is held by two flat plates, embodiments of the present invention are not limited in this way, and any holding scheme may be used. The present embodiment describes a case in which a PAT apparatus is used that adopts a scheme whereby an object is held by pressing one holding member against a body in such a manner that the object is pressurized and thus thinned, instead of causing two holding members to hold the object therebetween. In particular, the present embodiment describes a case in which a stretchable holding film is used as a holding member. The following describes an image processing apparatus according to the present embodiment, centering on differences from the first embodiment.

<Configuration of Image Diagnostic System 13>

Figure 13:
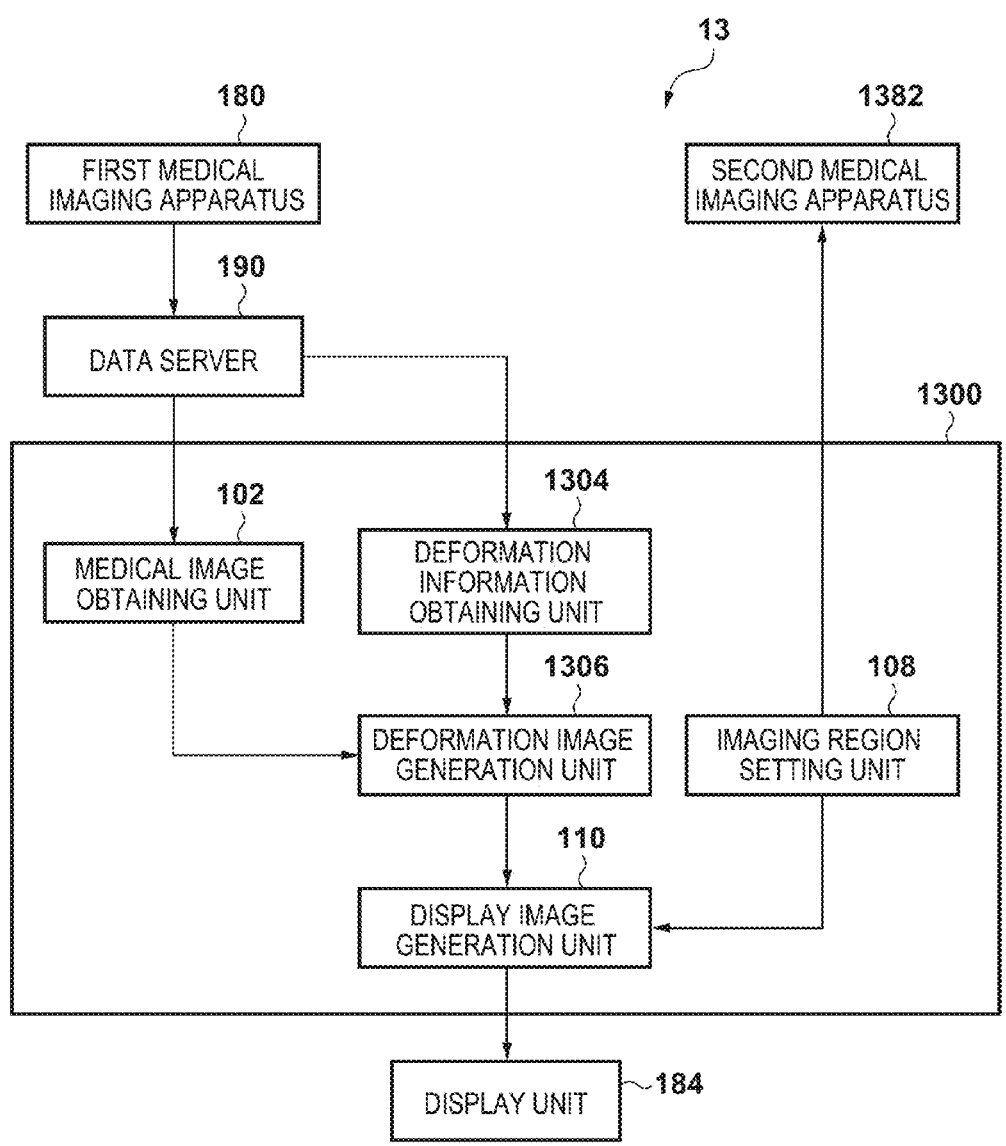
FIG. 13 shows functional configurations of an image diagnostic system and an image processing apparatus according to a third embodiment.

FIG. 13 shows a configuration of an image diagnostic system 13 according to the present embodiment. It should be noted that processing units that have the same functions as those in FIG. 1 are given the same numbers and signs thereas, and a description thereof is omitted.

The image diagnostic system 13 includes an image processing apparatus 1300, a first medical imaging apparatus 180, a second medical imaging apparatus 1382, a display unit 184, and a data server 190.

Figure 14:
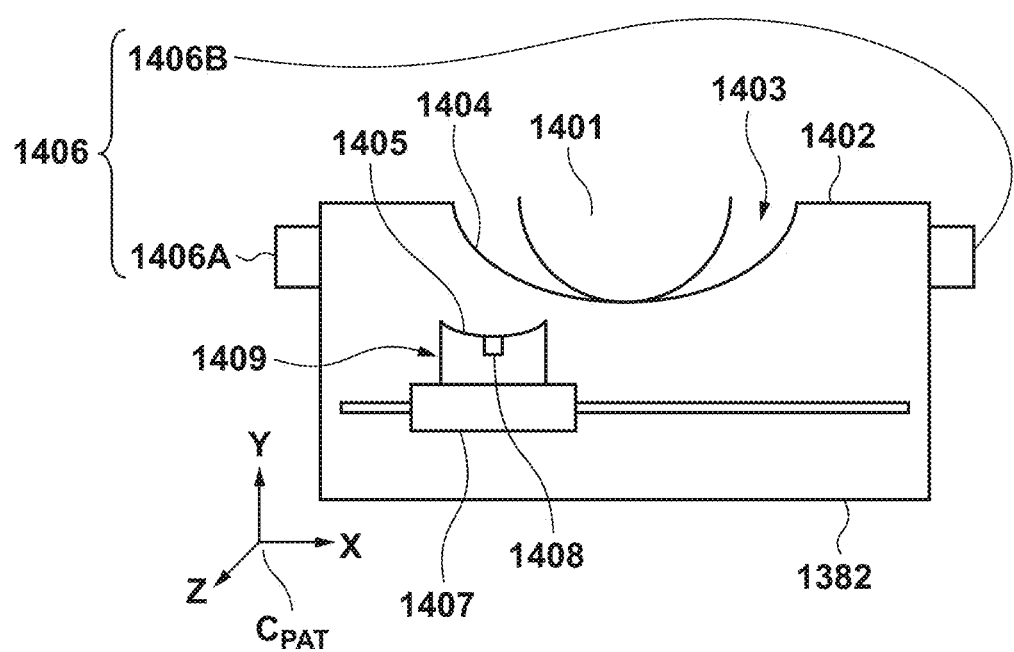
FIG. 14 is a schematic diagram showing a situation in which imaging is performed by a PAT apparatus according to the third embodiment.

The second medical imaging apparatus 1382 is a photoacoustic tomography imaging apparatus (PAT apparatus), and images a breast of an examinee by performing irradiation with near infrared ray pulses within a range of an imaging region set by a later-described imaging region setting unit 108 of the image processing apparatus 1300. FIG. 14 is a schematic diagram showing a situation in which imaging is performed by the second medical imaging apparatus 1382. The examinee takes a prone position on a bed on an upper surface 1402 of the second medical imaging apparatus 1382. An object, that is to say, a breast 1401 on one side is inserted into an opening 1403 of the upper surface 1402 of the second medical imaging apparatus 1382. At this time, in order for irradiation light in a direction from a nipple toward a pectoralis major to reach the internal parts of the breast, the breast is held in a state where it is pressurized by a transparent holding film 1404 in a direction from the nipple to the pectoralis major, and imaged in a state where the thickness thereof is reduced. Here, the holding film 1404 has a certain tension force, and has a planar shape before the breast 1401 is inserted. The holding film 1404 is placed in a deformed and warped state by the inserted breast 1401 applying pressure thereto. That is to say, in the present embodiment, a surface that comes into contact with the breast (a holding surface) is a curved surface.

The second medical imaging apparatus 1382 includes an imaging unit 1409 made up of an irradiation unit 1408 and an ultrasound probe 1405. The imaging unit 1409 is attached to a movable stage 1407 so as to image parts thereabove (from a viewpoint of the imaging unit 1409, a direction orthogonal to the upper surface 1402). The irradiation unit 1408 irradiates the object with near infrared ray pulses, which represent irradiation light. The ultrasound probe 1405 receives photoacoustic signals generated inside the object in response to irradiation of the near infrared ray pulses. That is to say, the second medical imaging apparatus 1382 images the object within a range of an imaging region while the movable stage 1407 is causing the imaging unit 1409 to move (scan) within the range of the imaging region. In the present embodiment, a PAT apparatus coordinate system C_PAT is defined as follows. A plane parallel to the upper surface 1402 is an XZ-plane, an axis representing a direction from the right hand to the left hand of the examinee is an X-axis, and an axis representing a direction from the feet to the head of the examinee is a Z-axis. Also, a normal direction of the upper surface 1402 is a Y-axis, and a direction from the anterior side to the posterior side of the examinee is a positive direction along the Y-axis. In addition, a lower end position on the right-hand side of the upper surface 1402 is the origin.

<Configurations of Functional Blocks of Image Processing Apparatus 1300>

The image processing apparatus 1300 is connected to the data server 190, the second medical imaging apparatus 1382, and the display unit 184. The image processing apparatus 1300 includes a medical image obtaining unit 102, a deformation information obtaining unit 1304, a deformation image generation unit 1306, an imaging region setting unit 108, and a display image generation unit 110.

The deformation information obtaining unit 1304 calculates and obtains deformation information by deforming and positioning an MRI image 200 with respect to the breast being pressurized by the holding film 1404, and outputs this deformation information to the deformation image generation unit 1306.

The deformation image generation unit 1306 generates a deformation MRI image by deforming the MRI image 200 into the shape of the breast being pressurized by the holding film 1404 based on the MRI image 200 and the deformation information, and outputs the deformation MRI image to the display image generation unit 110.

<Processing Executed by Image Processing Apparatus 1300>

Figure 15:
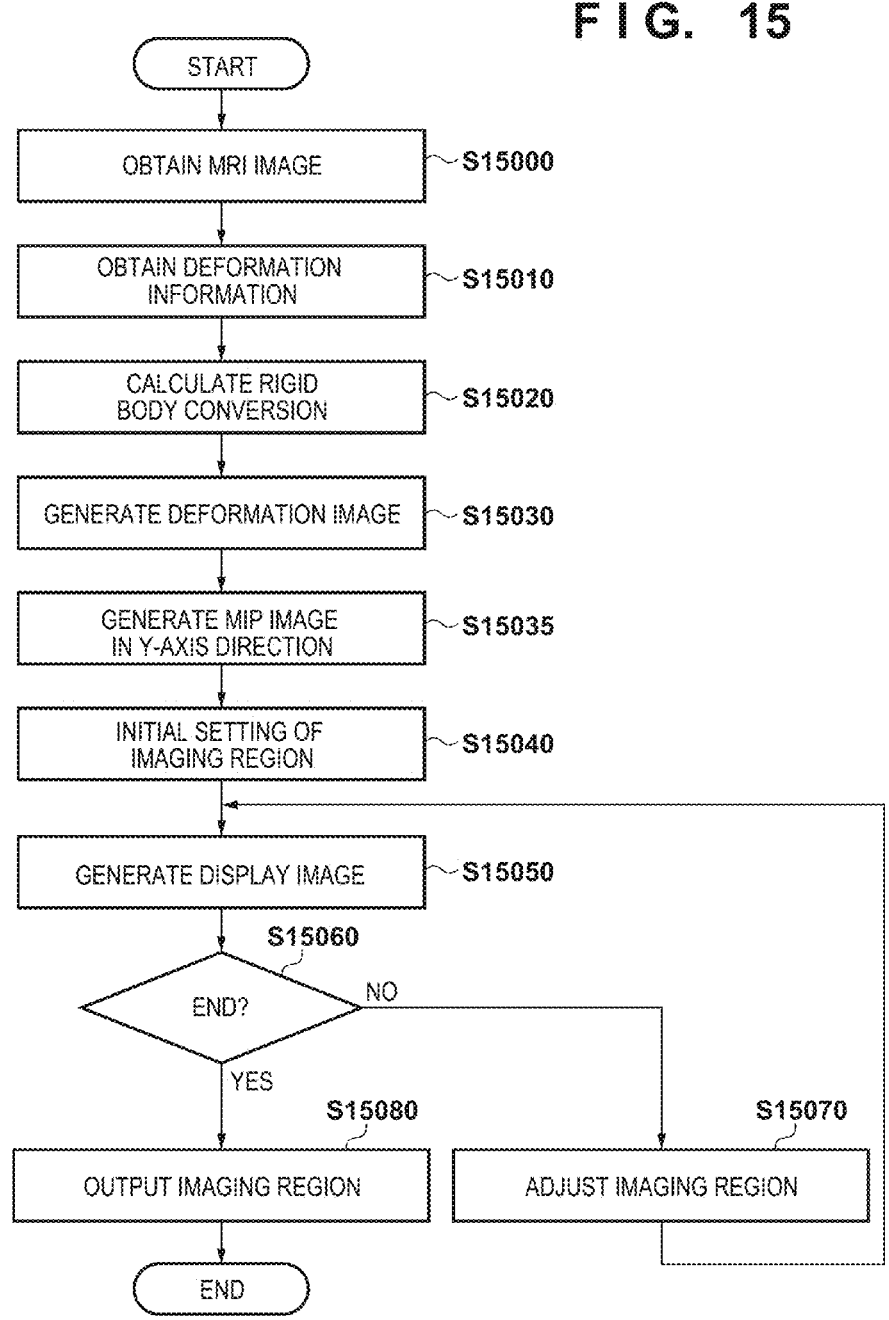
FIG. 15 is a flowchart showing a procedure of processing of the image processing apparatus according to the third embodiment.

Next, a description is given of a procedure of processing executed by the image processing apparatus 1300 according to the present embodiment with reference to a flowchart of FIG. 15. Compared to the processing executed by the image processing apparatus 100 according to the first embodiment, which has been described with reference to FIG. 5, in the processing executed by the image processing apparatus 1300 according to the present embodiment, processes of step S15010, step S15030, and step S15035 differ from corresponding processes of step S5010, step S5030, and step S5035.

[Step S15010: Obtainment of Deformation Information]

In step S15010, the deformation information obtaining unit 1304 calculates deformation information for deforming the MRI image 200 into the shape of the breast being pressurized by the holding film 1404. The present embodiment is based on the premise that the posture of the examinee in the PAT apparatus coordinate system C_PAT substantially matches the posture of the examinee in an MRI image coordinate system C_MRI. That is to say, it is assumed that the breast is compressed by the holding film 1404 substantially along a Y-axis direction of the MRI image coordinate system C_MRI. It is also assumed that the external shape of the breast 1401 and the shape of a pectoralis major in the MRI image 200 are input at the time of a physical deformation simulation.

Here, the external shape of the breast 1401 in the PAT apparatus coordinate system C_PAT can be obtained using, for example, one or more ranging apparatuses 1406 (in the example of FIG. 14, ranging apparatuses 1406A, 1406B) that are placed in a position in which the breast on the second medical imaging apparatus 1382 can be measured. That is to say, the external shape of the breast 1401 can be obtained by a user manually designating a breast region in range images of the breast captured by the ranging apparatuses 1406 using a non-illustrated mouse, keyboard, and the like. It is assumed that, at this time, the ranging apparatuses 1406 have already been calibrated in the PAT apparatus coordinate system C_PAT. Here, a nipple position in the PAT apparatus coordinate system C_PAT can also be obtained using the ranging apparatuses 1406. It should be noted that, in place of the external shape of the breast 1401, the shape of the holding film 1404 may be obtained and used with the use of the ranging apparatuses 1406.

Also, the shape of the pectoralis major in the MRI image coordinate system C_MRI can be obtained by applying a known image analysis method or the user's manual designation using the non-illustrated mouse, keyboard, and the like with respect to the MRI image 200.

[Step S15030: Generation of Deformation Image]

In step S15030, the deformation image generation unit 1306 generates a deformation MRI image that has been deformed into the shape of the breast being pressurized by the holding film 1404 based on the MRI image 200. Comparing a pre-deformation breast shape with a post-deformation breast shape, pressurization in a Y-axis direction of the PAT apparatus coordinate system C_PAT has caused the breast region to extend along the XZ-plane and to compress in the Y-axis direction.

[Step S15035: Generation of MIP Image (Conversion Image) in Y-axis Direction]

In step S15035, the deformation image generation unit 1306 generates a conversion image that has been converted in accordance with an imaging region. For example, a deformation MRI_MIP image 1600 shown in FIG. 16 is generated by projecting a maximum pixel value in the Y-axis direction of the PAT apparatus coordinate system C_PAT onto the XZ-plane (Y=0) based on the deformation MRI image generated in step S15030.

[Step S15050: Generation of Display Image]

Figure 16:
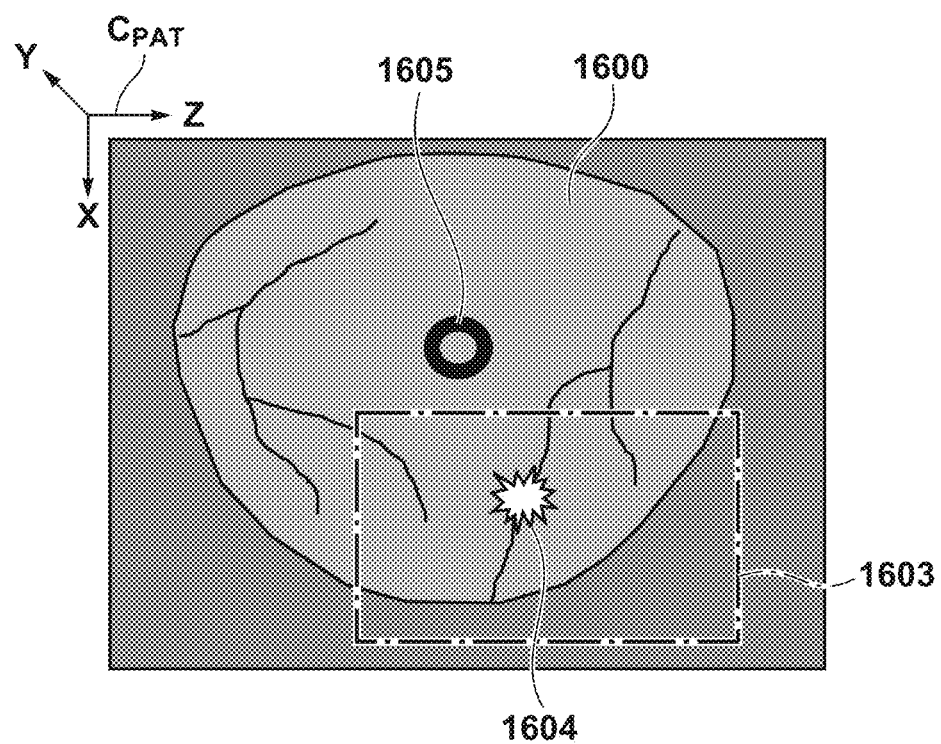
FIG. 16 is a schematic diagram showing an example of a display image according to the third embodiment.

In step S15050, the display image generation unit 110 generates a display image by overlapping an imaging region 1603 shown in FIG. 16 over the deformation MRI_MIP image 1600 along the Y-axis direction generated in step S15035, and outputs the display image to the display unit 184.

[Step S15070: Adjustment of Imaging Region]

In step S15070, based on a user operation, the imaging region setting unit 108 adjusts the imaging region of the second medical imaging apparatus 1382 on the display image. Specifically, on an image displayed on the imaging region setting screen of the display unit 184, the user manually adjusts a range of the set imaging region 1603 (two-dimensional rectangular region) using the non-illustrated mouse, keyboard, and the like. Based on information that the user has visually confirmed on the displayed image, the user adjusts the imaging region 1603 such that it includes, for example, the entirety of a tumor 1604. It should be noted that 1604 denotes a tumor in the deformation MRI_MIP image, and 1605 denotes a nipple in the deformation MRI_MIP image. Thereafter, processing returns to step S15050.

As described above, the image processing apparatus 1300 according to the present embodiment includes the medical image obtaining unit 102 that obtains a medical image (the MRI image 200) of an object (e.g., a breast) in a first shape state (an unheld state), a deformation information obtaining unit 1304 that obtains deformation information indicating deformation of the object from the first shape state (the unheld state) to a second shape state (a held state in which the object is held by the holding film 1404), the imaging region setting unit 108 that sets an imaging region of the object in the second shape state, the deformation image generation unit 1306 that generates a conversion image (a deformation MRI_MIP image) by converting a medical image deformed based on the deformation information in accordance with the imaging region, and the display image generation unit 110 that generates a display image by overlapping the conversion image (the deformation MRI_MIP image) and the imaging region.

In this way, when setting an imaging region of a PAT image, the image processing apparatus according to the present embodiment can refer to an MRI image in which a region of attention, such as a tumor, inside the object is rendered. This makes it possible to set the imaging region such that a region of attention, such as a tumor, inside the object can be imaged appropriately. The present embodiment also allows for reduction in the burden of the examinee compared to a configuration in which a breast is pressurized from both sides.

First Modification Example of Third Embodiment

While the present embodiment has described an exemplary case in which an object is held by one holding member in such a manner that the object is pressurized and thus thinned, embodiments of the present invention are not limited in this way. For example, a breast may be held in a thinned state by placing the breast in an arch-shaped or bowl-shaped container (holding container) serving as a holding member. If the shape of the holding container is known, it is sufficient to estimate deformation of an MRI image such that the shape of the object in the MRI image matches the shape of the holding container. On the other hand, if the shape of the holding container is unknown, or if there is a matching agent or a matching liquid between the holding container and the object, deformation of the MRI image may be estimated in accordance with the external shape of a side surface of the breast obtained by a ranging apparatus. Also, the breast may be held by a planar holding plate pressed thereagainst from a direction of a nipple. In this case, a combination of the external shape of a side surface of the breast obtained by a ranging apparatus and the planar shape of the breast may be used as the external shape of the breast.

Second Modification Example of Third Embodiment

Figure 17:
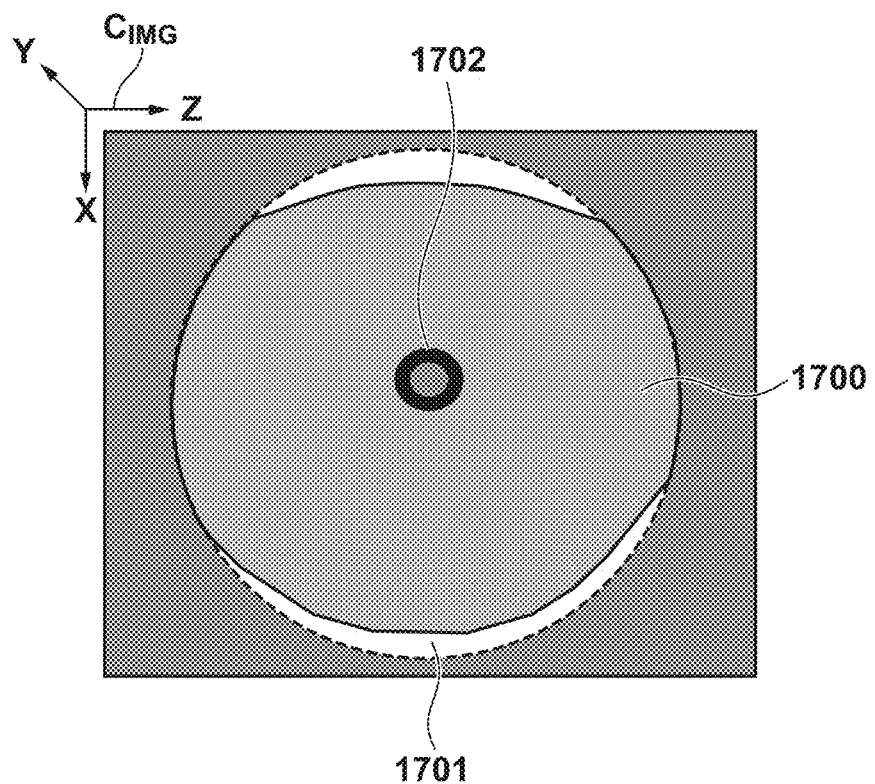
FIG. 17 is a schematic diagram showing an appearance image captured by a camera mounted on a PAT apparatus according to a second modification example of the third embodiment.

While the present embodiment has described an exemplary case in which an imaging region is set on an imaging region setting screen displaying a deformation MRI image similarly to the first embodiment, an imaging region may be set on an appearance image of a breast captured by a camera mounted on the PAT apparatus similarly to the second embodiment. It is sufficient to place this camera, for example, in a position in which the appearance of the breast can be imaged from a front side of the examinee through the holding film 1204, and to calibrate this camera in the PAT apparatus coordinate system C_PAT. FIG. 17 is a schematic diagram showing an appearance image 1700 of the breast captured by the camera from the front side of the examinee. CIMG denotes an appearance image coordinate system, 1701 denotes an opening 1703 in the appearance image, and 1705 denotes a nipple in the appearance image.

Figure 18:
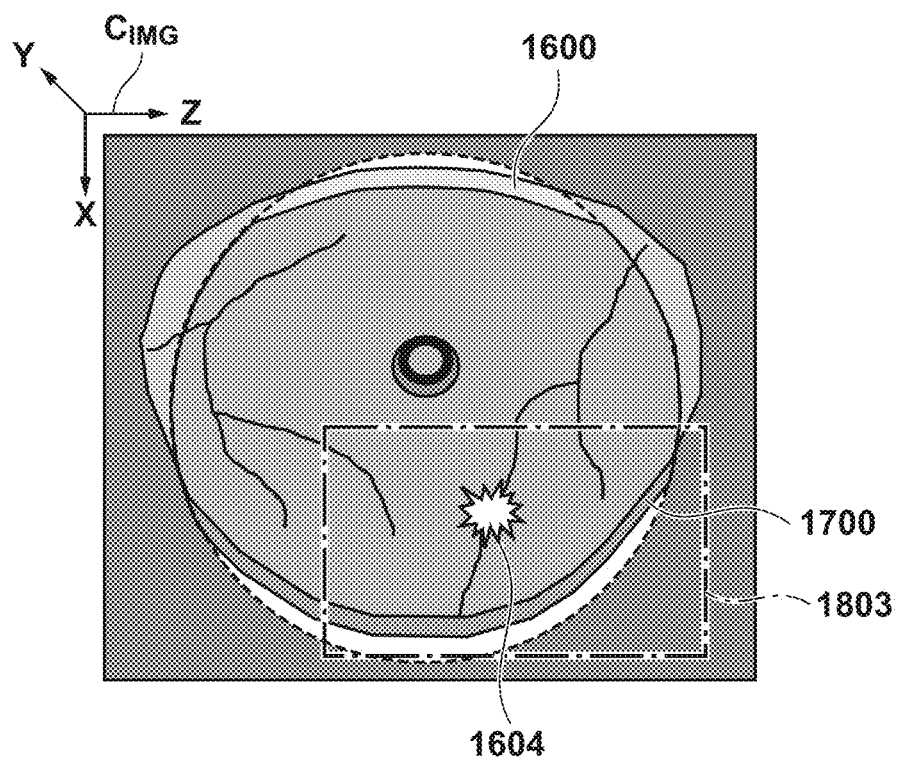
FIG. 18 is a schematic diagram showing an example of a display image according to a second modification example of the third embodiment.

It is assumed that, in the present modification example, the appearance image 1700 lies on an XZ-plane at Y=0. FIG. 18 is a schematic diagram showing a display image in which a deformation MRI_MIP image 1600 along the Y-axis direction is overlapped over the appearance image 1700. On this display image, the user can manually set an imaging region 1803 such that it includes, for example, the entirety of the tumor 1604 in the deformation MRI_MIP image similarly to the second embodiment.

Third Modification Example of Third Embodiment

While the present embodiment has described an exemplary case in which the imaging region 1803 is a two-dimensional rectangular region, embodiments of the present invention are not limited in this way. For example, the imaging region 1803 may be a region enclosed by a circle or an ellipse depending on a method in which the movable stage 1407 causes the imaging unit 1409 to move (scan). Alternatively, it may be a region enclosed by any closed curve.

The present invention makes it possible to set an imaging region such that a region of attention inside an object can be imaged appropriately.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2014-006214, filed Jan. 16, 2014, and 2014-230104, filed Nov. 12, 2014, which are hereby incorporated by reference herein in their entirety.

The invention claimed is:

1. An image processing apparatus, comprising at least one processor and memory coupled to each other and cooperating to act as:
   a medical image obtaining unit configured to obtain a first medical image of an object in a first shape state;
   a deformation information obtaining unit configured to obtain deformation information indicating deformation of the object from the first shape state to a second shape state;
   a deformation image generating unit configured to generate a deformation image by deforming the first medical image based on the deformation information and to generate a conversion image for setting a region to be imaged by converting the deformation image;
   an imaging region setting unit configured to set the region to be imaged of the object in the second shape state based on a user operation on the conversion image, before taking a second medical image of the object in the second shape state;
   a display control unit configured to cause a display unit to display the conversion image and the region to be imaged; and
   an imaging region outputting unit configured to output information of the region to be imaged to a medical imaging apparatus in order to take the second medical image by using the medical imaging apparatus based on the information of the region to be imaged.

2. The image processing apparatus according to claim 1, wherein the imaging region setting unit adjusts the region to be imaged based on a user operation on the conversion image.

3. The image processing apparatus according to claim 1, wherein the deformation image generating unit generates a volume rendering image or a maximum value projection image of the deformation image in the second shape state as the conversion image.

4. The image processing apparatus according to claim 1, wherein the first medical image is an MRI image of the object.

5. The image processing apparatus according to claim 1, wherein the at least one processor and memory further cooperate to act as an appearance image obtaining unit configured to obtain an appearance image of the object in the second shape state,
   a space for setting the region to be imaged is a plane of the appearance image, and
   the display control unit causes the display unit to display the appearance image on which the conversion image is superimposed.

6. The image processing apparatus according to claim 5, wherein the at least one processor and memory further cooperate to act as an inappropriate region setting unit configured to set an inappropriate region based on a user operation on the appearance image, the inappropriate region being inappropriate for imaging of the object in the second shape state, and
   the display control unit causes the display unit to display the inappropriate region superimposed on the appearance image.

7. An image diagnostic system, comprising:
   the image processing apparatus according to claim 1; and
   the medical imaging apparatus that takes the second medical image.

8. An image diagnostic system, comprising:
   the image processing apparatus according to claim 5;
      the medical imaging apparatus that takes the second medical image; and
      an appearance imaging apparatus that takes the appearance image.

9. An image processing method, comprising:
   obtaining a first medical image of an object in a first shape state;
   obtaining deformation information indicating deformation of the object from the first shape state to a second shape state;
   generating a deformation image by deforming the first medical image based on the deformation information and generating a conversion image for setting a region to be imaged by converting the deformation image;
   setting the region to be imaged of the object in the second shape state based on a user operation on the conversion image, before taking a second medical image of the object in the second shape state;
   causing a display unit to display the conversion image and the region to be imaged; and
   outputting information of the region to be imaged to a medical imaging apparatus in order to take the second medical image by using the medical imaging apparatus based on the information of the region to be imaged.

10. A non-transitory computer-readable storage medium storing a program for causing a computer to execute an image processing method, said image processing method comprising:
   obtaining a first medical image of an object in a first shape state;
   obtaining deformation information indicating deformation of the object from the first shape state to a second shape state;
   generating a deformation image by deforming the first medical image based on the deformation information and generating a conversion image for setting a region to be imaged by converting the deformation image;
   setting the region to be imaged of the object in the second shape state based on a user operation on the conversion image, before taking a second medical image of the object in the second shape state;
   causing a display unit to display the conversion image and the imaging region; and
   outputting information of the region to be imaged to a medical imaging apparatus in order to take the second medical image by using the medical imaging apparatus based on the information of the region to be imaged.

11. The image processing apparatus according to claim 1, wherein the information of the region to be imaged is information which is obtained by adding a predetermined margin to the region to be imaged.

12. The imaging processing apparatus according claim 11, wherein the predetermined margin is information related to error of the deformation.

13. The image processing apparatus according to claim 2, wherein the deformation image generating unit generates a volume rendering image or a maximum value projection image of the deformation image in the second shape state as the conversion image.

14. The image processing apparatus according to claim 2, wherein the first medical image is an MRI image of the object.

15. The image processing apparatus according to claim 3, wherein the first medical image is an MRI image of the object.

16. The image processing apparatus according to claim 13, wherein the first medical image is an MRI image of the object.

17. The image processing apparatus according to claim 2, wherein the at least one processor and memory further cooperate to act as an appearance image obtaining unit configured to obtain an appearance image of the object in the second shape state,
- a space for setting the region to be imaged is a plane of the appearance image, and
- the display control unit causes the display unit to display the appearance image on which the conversion image is superimposed.

18. The image processing apparatus according to claim 3, wherein the at least one processor and memory further cooperate to act as an appearance image obtaining unit configured to obtain an appearance image of the object in the second shape state,
- a space for setting the region to be imaged is a plane of the appearance image, and
- the display control unit causes the display unit to display the appearance image on which the conversion image is superimposed.

19. The image processing apparatus according to claim 13, wherein the at least one processor and memory further cooperate to act as an appearance image obtaining unit configured to obtain an appearance image of the object in the second shape state,
- a space for setting the region to be imaged is a plane of the appearance image, and
- the display control unit causes the display unit to display the appearance image on which the conversion image is superimposed.

* * * * *